US012810967B2

(12) United States Patent
Choi et al.

(10) Patent No.: US 12,810,967 B2
(45) Date of Patent: Nov. 24, 2026

(54) ELECTRONIC DEVICE FOR IMPLEMENTING POLYMER QUALITY PREDICTION AND CONTROL SYSTEM AND CONTROL METHOD THEREOF

(71) Applicant: INEEJI Co., Ltd., Seongnam-si (KR)

(72) Inventors: Chan Hee Choi, Yongin-si (KR); Chai Hyuk Lee, Seongnam-si (KR); Soo Jeong Han, Busan (KR)

(73) Assignee: INEEJI Co. Ltd., Seongnam-si (KR)

( * ) Notice: Subject to any disclaimer, the term of this patent is extended or adjusted under 35 U.S.C. 154(b) by 349 days.

(21) Appl. No.: 18/715,468

(22) PCT Filed: Jan. 30, 2024

(86) PCT No.: PCT/KR2024/001410
§ 371 (c)(1),
(2) Date: May 31, 2024

(87) PCT Pub. No.: WO2024/162738
PCT Pub. Date: Aug. 8, 2024

(65) Prior Publication Data

US 2026/0155214 A1 Jun. 4, 2026

(30) Foreign Application Priority Data

Jan. 31, 2023 (KR) ........................ 10-2023-0012294

(51) Int. Cl.
*G16C 20/20* (2019.01)
*G16C 20/70* (2019.01)
(Continued)

(52) U.S. Cl.
CPC ............. *G16C 20/20* (2019.02); *G16C 20/70* (2019.02); *G16C 20/80* (2019.02)

(58) Field of Classification Search
CPC ........ G16C 20/20; G16C 20/30; G16C 20/70; G16C 20/80; G06N 3/02
See application file for complete search history.

(56) References Cited

U.S. PATENT DOCUMENTS 12,159,692 B2 * 12/2024 Fabian Galvez ...... G16C 60/00
12,592,977 B2 * 3/2026 Agarwal ............. H04L 65/4061
(Continued)

FOREIGN PATENT DOCUMENTS

KR 10-2018-0022030 A 3/2018
KR 10-2021-0060467 A 5/2021
WO 2022/242843 A1 11/2022

OTHER PUBLICATIONS

International Search Reported dated May 1, 2024 issued in Application No. PCT/KR2024/001410.
(Continued)

*Primary Examiner* — Tan Q Nguyen
(74) *Attorney, Agent, or Firm* — USX IP LLC

(57) ABSTRACT

An electronic device for implementing a quality prediction and control system includes a communication interface, a memory for storing a trained neural network model and process history information of a polymer production apparatus, and one or more processors for identifying predicted process information corresponding to a third time point when a preset time elapses from a second time point based on the process history information and process information corresponding to the second time point when process information corresponding to the second time point is received from the polymer production apparatus through the communication interface, inputting the received process information corresponding to the second time point and the identified predicted process information corresponding to the third time point to a trained neural network model to acquire predicted quality information of the polymer corre-
(Continued)

sponding to the third time point, and providing guide information including the acquired predicted quality information.

11 Claims, 9 Drawing Sheets

(51) Int. Cl.
*G16C 20/80* (2019.01)
*G06N 3/02* (2006.01)

(56) References Cited

U.S. PATENT DOCUMENTS

| | | | | |
|---|---|---|---|---|
| 2019/0041835 | A1* | 2/2019 | Cella | G05B 19/4183 |
| 2022/0068440 | A1* | 3/2022 | Mrziglod | G16C 20/70 |
| 2023/0029474 | A1* | 2/2023 | Wade | G16C 20/10 |

OTHER PUBLICATIONS

Andy Yen-Di Tsen, et al., "Predictive Control of Quality in Batch Polymerization Using Hybrid ANN Models", AIChE Journal, Feb. 1996, vol. 42, No. 2, pp. 455-465 (11 pages).

Kelvin Naidoo, et al,"Experiences with Nonlinear MPC in Polymer Manufacturing", Assessment and Future Directions, 2007, pp. 383-398 (16 pages).

* cited by examiner

ELECTRONIC DEVICE FOR IMPLEMENTING POLYMER QUALITY PREDICTION AND CONTROL SYSTEM AND CONTROL METHOD THEREOF

CROSS REFERENCE TO RELATED APPLICATIONS

This application is a National Stage of International Application No. PCT/KR2024/001410 filed Jan. 30, 2024, claiming priority based on Korean Patent Application No. 10-2023-0012294 filed Jan. 31, 2023.

TECHNICAL FIELD

The present disclosure relates to an electronic device for implementing a polymer quality prediction and control system and a control method thereof, and more particularly, to an electronic device for predicting the quality of a polymer using preprocessed data and a trained neural network model and a control method thereof.

BACKGROUND ART

With the development of electronic technology, various types of electronic devices are being developed and spread, and recently, technology development for electronic devices that provide services to users and the like is becoming more active.

Meanwhile, a polymer refers to a polymer in which one or more monomers are repeatedly connected. A polymer production process according to the present disclosure is a process of acquiring polyethylene, which is a polymer, for example, a polyolefin elastomer (POE), by polymerizing ethylene, octene, or butene in the presence of a catalyst corresponding to the monomer. Polymers are classified into product groups depending on their melting index and density. The melting index or density is an indicator that is affected by the amount of raw materials input to the production process, a ratio of raw materials, or reaction temperature, and represents the quality of polymers.

Meanwhile, the quality and yield of a polymer acquired through a chemical reaction between monomers may vary due to disturbances that cannot be controlled or measured. For example, due to the nature of the polymerization reaction, even when the same conditions or the same raw materials are input, the melting index and density of the acquired polymer may be different. In addition, in the case of a recovery process for raw materials in which no reaction has occurred, the amount of raw materials re-input to the reaction is not measured, so it is difficult to predict the exact quality of the acquired polymer.

DISCLOSURE

Technical Problem

The present disclosure provides an electronic device for accurately predicting the quality of a produced polymer by preprocessing information on a polymer production process and inputting the preprocessed information to a trained neural network model, and a control method thereof.

Technical Solution

According to an embodiment of the present disclosure, an electronic device for implementing a quality prediction and control system may include a communication interface, a memory that stores a trained neural network model and process history information of a polymer production apparatus, and one or more processors that identify predicted process information corresponding to a third time point when a preset time elapses from a second time point based on the process history information and process information corresponding to the second time point when the process information corresponding to the second time point is received from the polymer production apparatus through the communication interface.

The one or more processors may input the received process information corresponding to the second time point and the identified predicted process information corresponding to the third time point to the trained neural network model to acquire predicted quality information of a polymer corresponding to the third time point.

The one or more processors may provide guide information including the acquired predicted quality information.

According to another embodiment of the present disclosure, a control method of an electronic device for implementing a quality prediction and control system may include: identifying predicted process information corresponding to a third time point when a preset time elapses from a second time point based on process history information of a polymer production apparatus and process information corresponding to the second time point when the process information corresponding to the second time point is received from the polymer production apparatus.

The control method may include inputting the received process information corresponding to the second time point and the identified predicted process information corresponding to the third time point to a trained neural network model to acquire predicted quality information of a polymer corresponding to the third time point.

The control method may include providing guide information including the acquired predicted quality information.

According to still another embodiment of the present disclosure, in a non-transitory computer-readable recording medium for storing computer instructions causing an electronic device for implementing a quality prediction and control system to perform operations when executed by a processor of the electronic device, the operations may include identifying predicted process information corresponding to a third time point when a preset time elapses from a second time point based on process history information of a polymer production apparatus and process information corresponding to the second time point when the process information corresponding to the second time point is received from the polymer production apparatus.

The operations may include inputting the received process information corresponding to the second time point and the identified predicted process information corresponding to the third time point to a trained neural network model to acquire predicted quality information of a polymer corresponding to the third time point.

The operations may include providing guide information including the acquired predicted quality information.

Advantageous Effects

According to the above-described example, it is possible to accurately predict the quality of the polymer acquired through the polymer production process and provide the guide information to the user based on the predicted quality.

MODE FOR INVENTION

Figure 1:
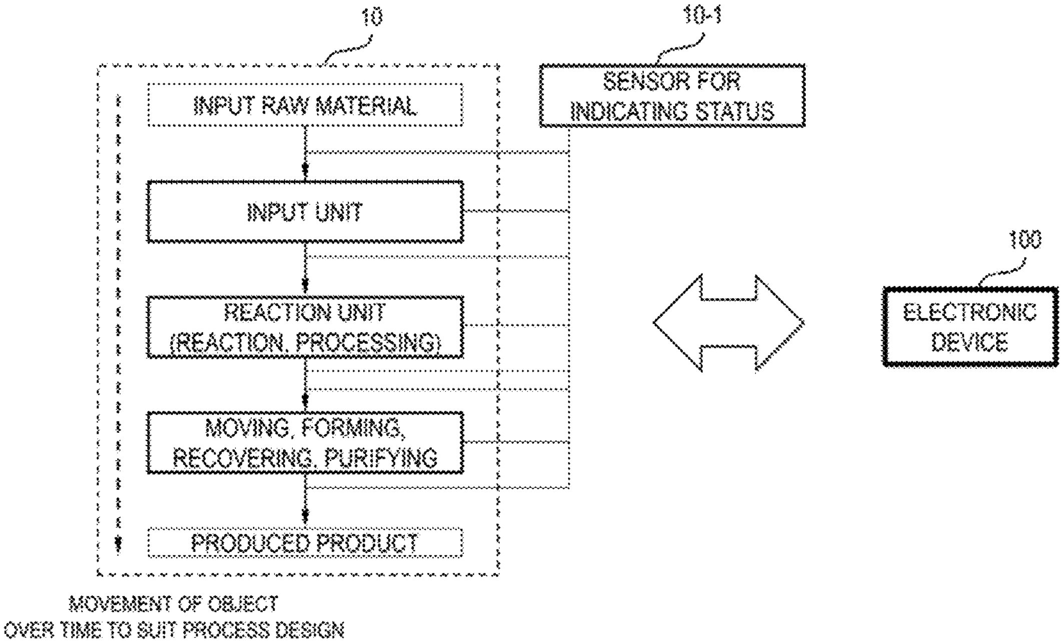
FIG. 1 is a diagram schematically illustrating a control method of an electronic device according to an embodiment.

Hereinafter, the present disclosure will be described in detail with reference to the accompanying drawings.

Terms used in the present specification will be briefly described, and the present disclosure will be described in detail.

General terms that are currently widely used were selected as terms used in embodiments of the present disclosure in consideration of functions in the present disclosure, but may be changed depending on the intentions of those skilled in the art or legal precedents, the emergence of new technology, and the like. In addition, in certain cases, there may be terms arbitrarily chosen by an applicant. In these cases, the meaning of such terms will be described in detail in the relevant description of the present disclosure. Therefore, the terms used in the present disclosure should be defined on the basis of the meaning of the terms and the contents throughout the present disclosure rather than simple names of the terms.

In the present disclosure, the expression "have," "may have," "include," "may include," or the like indicates the presence of a corresponding feature (for example, a numerical value, a function, an operation, a component such as a part, or the like), and does not exclude the presence of an additional feature.

The expression "at least one of A and/or B" is to be understood to indicate "A" or "B" or "any one of A and B."

The terms "first," "second," "$1^{st}$," or "$2^{nd}$" and the like used in the present disclosure may indicate various components regardless of the order and/or importance of the components are only used in order to distinguish one component from another component and do not limit the corresponding components.

When it is stated that a component (for example, a first component) is (operatively or communicatively} coupled with/to or is connected to another component (for example, a second component), it is to be understood that the first component is directly coupled to the second component or may be coupled to the second component through still another component (for example, a third component).

Singular forms are intended to include plural forms unless the context clearly indicates otherwise. It should be further understood that the terms "include" and "configured" used in the present specification specify the presence of features, numerals, steps, operations, components, parts stated in the present specification, or combinations thereof, but do not preclude the presence or addition of one or more other features, numerals, steps, operations, components, parts, or combinations thereof.

In the disclosure, a "module" or a "~unit" may perform at least one function or operation and may be implemented by hardware or software or implemented by a combination of hardware and software. In addition, a plurality of "modules" or a plurality of "~units" may be integrated in at least one module and implemented by at least one processor (not illustrated) except for a "module" or a "~unit" that needs to be implemented by specific hardware.

An electronic device according to an embodiment of the present disclosure may include an artificial intelligence model (or artificial neural network model or training network model) composed of at least one neural network layer. The artificial neural network may include a deep neural network (DNN), and examples of the artificial neural network may include a convolutional neural network (CNN), a recurrent neural network (RNN), a restricted Boltzmann machine (RBM), a deep belief network (DBN), a bidirectional recurrent deep neural network (BRDNN), a deep Q-Network, and the like, but are not limited thereto.

In addition, in this specification, "parameters" are values used in a calculation process of each layer forming a neural network and may include, for example, a weight used when applying an input value to a predetermined calculation equation. In addition, the parameter may be expressed in a matrix form. The parameters are values set as a result of training and may be updated through separate training data, if necessary.

Meanwhile, the parameters described below refer to variables corresponding to at least one layer constituting a neural network model and at least one node included in the layer.

FIG. 1 is a diagram schematically illustrating a control method of an electronic device according to an embodiment.

According to FIG. 1, according to an embodiment, when raw materials are input, a polymer production apparatus 10 may produce polymers (production products) based on the raw materials. The polymer production apparatus 10 may include a plurality of production units including an input unit, a reaction unit, a moving unit, a forming unit, a recovery unit, and a purification unit. Meanwhile, the polymer production apparatus 10 may include a sensor 10-1 indicating a plurality of statuses, and the sensor 10-1 may be included in each of the plurality of production units.

According to an embodiment, the sensor 10-1 may acquire information on the amount of raw materials and ratio of a plurality of types of input raw materials (e.g., hydrogen, catalyst, butene, octene, etc.) input to the polymer production apparatus 10. In addition, information on a process status of the polymer production apparatus 10, for example, at least one of information on the pressure, temperature, flow rate, and power amount of the production unit of the polymer production apparatus 10 may be acquired. Alternatively, the sensor 10-1 may also acquire the information on the polymer produced by the polymer production apparatus 10.

Meanwhile, according to an embodiment, an electronic device 100 may receive information acquired through a sensor and predict the quality of polymer produced at a preset time based on the received information. Here, the quality may be, for example, the melting index (MI), density, or melt flow index (MFR) type of the produced polymer.

Hereinafter, various embodiments of a method of accurately predicting the quality of polymer produced in the polymer production apparatus 10 by preprocessing information generated in the polymer production process and inputting the preprocessed information to a trained neural network model will be described.

Figure 2:
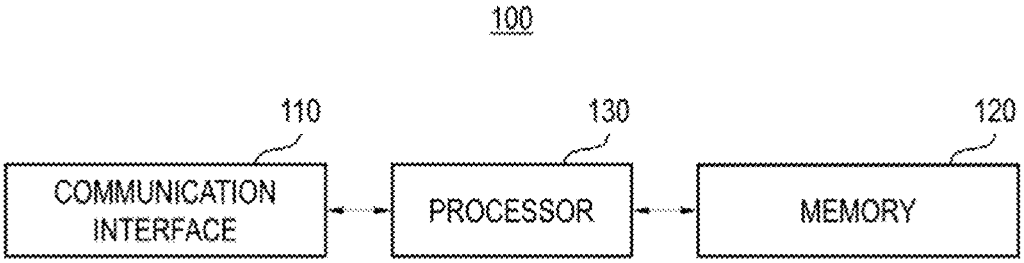
FIG. 2 is a block diagram illustrating a configuration of an electronic device according to an embodiment.

FIG. 2 is a block diagram illustrating a configuration of an electronic device according to an embodiment.

Referring to FIG. 2, the electronic device 100 includes a communication interface 110, a memory 120, and one or more processors 130.

According to an embodiment, the electronic device 100 may be implemented by a device that processes data like a server and communicates with an external device, but is not limited thereto. For example, the electronic device 100 may be implemented by various devices such as a smart TV, a tablet, a monitor, a smart phone, a desktop computer, and a laptop computer. The electronic device 100 according to the embodiment of the present disclosure is not limited to the above-described devices, and the electronic device 100 may be implemented by the electronic device 100 having two or more functions of the above-described devices.

Meanwhile, the electronic device 100 may communicate with an external device and an external server in various ways. According to an embodiment, a communication module for communication with the external device and external server may be implemented in the same way. For example, the electronic device 100 may communicate with an external device using a Bluetooth module and may also communicate with an external server using the Bluetooth module.

According to another embodiment, the communication module for communication with the external device and external server may be implemented separately. For example, the electronic device 100 may communicate with an external device using a Bluetooth module and communicate with an external server using an Ethernet modem or a wireless fidelity (Wi-Fi) module.

Meanwhile, the external device may be implemented by at least one of the polymer production apparatus 10 or a control engine for controlling the polymer production apparatus 10, but is not limited thereto.

The communication interface 110 may input and output various types of data. For example, the communication interface 110 may transmit and receive various types of data to and from an external device (e.g., source device), an external storage medium (e.g., USB memory), an external server (e.g., web hard), etc., through communication methods such as AP-based Wi-Fi (wireless LAN network), Bluetooth, ZigBee, a wired/wireless local area network (LAN), a wide area network (WAN), Ethernet, IEEE 1394, a high-definition multimedia interface (HDMI), a universal serial bus (UBS), a mobile high-definition link (MHL), an audio engineering society/European broadcasting union (AES/EBU), an optical method, coaxial method, etc.

According to an example, the communication interface 110 may include a Bluetooth low energy (BLE) module. BLE refers to a Bluetooth technology that enables transmission and reception of low-power, low-capacity data in the 2.4 GHz frequency band with a reach radius of approximately 10 m. However, it is not limited thereto, and the communication interface 110 may also include a Wi-Fi communication module. That is, the communication interface 110 may include at least one of a BLE module or a Wi-Fi communication module.

According to an example, the communication interface 110 may use different communication modules to communicate with an external device, such as a remote control, and an external server. For example, the communication interface 110 may use at least one of an Ethernet module or a Wi-Fi module to communicate with an external server, and may use a Bluetooth module to communicate with an external device such as a remote control. However, this is only an example, and the communication interface 110 may use at least one of various communication modules in a case in which it communicates with a plurality of external devices or external servers.

According to an embodiment, one or more processors 130 may receive process information from the polymer production apparatus 10 through the communication interface 110.

The memory 120 may store data necessary for various embodiments. The memory 120 may be implemented in the form of a memory embedded in the electronic device 100 or the form of a memory detachable from the electronic device 100, depending on the data storage purpose. For example, data for driving the electronic device 100 may be stored in a memory embedded in the electronic device 100, and data for an expansion function of the electronic device 100 may be stored in a memory attachable to and detachable from the electronic device 100.

Meanwhile, the memory embedded in the electronic device 100 may be implemented by at least one of, for example, a volatile memory (for example, a dynamic random access memory (DRAM), a static RAM (SRAM), a synchronous dynamic RAM (SDRAM), or the like), a non-volatile memory (for example, a one time programmable read only memory (OTPROM), a programmable ROM (PROM), an erasable and programmable ROM (EPROM), an electrically erasable and programmable ROM (EEPROM), a mask ROM, a flash ROM, a flash memory (for example, a NAND flash, a NOR flash, or the like), a hard drive, and a solid status drive (SSD)). In addition, the memory detachable from the electronic device 100 may be implemented in the form of a memory card (e.g., compact flash (CF), secure digital (SD), micro secure digital (Micro-SD), mini secure digital (Mini-SD), extreme digital (xD), multi-media card (MMC), etc.), an external memory (e.g., USB memory) connectable to a USB port, etc.

Meanwhile, according to an embodiment, the memory 120 may store the trained neural network model and process history information of the polymer production apparatus. Here, according to an example, the process history information may include history information on the amount of raw materials input to the polymer production apparatus 10, the amount of polymer produced by the polymer production apparatus 10, and the process status of the polymer production apparatus 10. For example, the process history information may include input raw material information, polymer production information, process status information, and quality information on the produced polymer corresponding to each of a plurality of time points before a second time point.

Meanwhile, the trained neural network model is a trained neural network model that outputs quality information when the process history is input. This will be described in detail with reference to FIG. 4.

One or more processors 130 (hereinafter, referred to as processors) are electrically connected to the communication interface 110 and the memory 120 and control the overall operation of the electronic device 100. The processor 130 may include one or a plurality of processors. Specifically, the processor 130 may perform an operation of the electronic device 100 according to various embodiments of the present disclosure by executing at least one instruction stored in the memory 120.

According to an embodiment, the processor 130 may be implemented by a digital signal processor (DSP), a microprocessor, a graphics processing unit (GPU), an artificial intelligence (AI) processor, a neural processing unit (NPU), or a time controller (TCON) that processes a digital image signal. However, it is not limited thereto, and the processor 130 may include one or more of a central processing unit (CPU), a micro controller unit (MCU), a micro processing unit (MPU), a controller, an application processor (AP), a communication processor (CP), and an ARM processor, or may be defined by these terms. In addition, the processor 130 may be implemented by a system-on-chip (SoC) or large scale integration (LSI) in which a processing algorithm is embedded, or may be implemented in the form of an application specific integrated circuit (ASIC) or a field programmable gate array (FPGA).

According to an embodiment, the processor 130 may be implemented by a DSP, a microprocessor, or a TCON. However, the processor 130 is not limited thereto and may include one or more of a CPU, a MCU, an MPU, a controller, an AP, a CP, and an ARM processor, or may be defined by these terms. In addition, the processor 130 may be implemented by an SoC or LSI in which a processing algorithm is embedded, or may be implemented in the form of a FPGA.

According to an embodiment, one or more processors 130 may receive process information corresponding to the second time point from the polymer production apparatus 10 (not illustrated) through the communication interface 110.

According to an example, the second time point may be a current time point, but is not limited thereto. The process information may include at least one of information on raw materials input to the polymer production apparatus 10, information on the amount of polymer produced (or acquired) in the polymer production apparatus 10, and information on the process status of the polymer production apparatus 10. Here, the information on input raw materials refers to the amount of raw materials input to the polymer production apparatus 10 during a preset time period, and the information on produced polymer refers to the amount of polymer produced by the polymer production apparatus 10 during a preset time period. The information on the process status may include information on a flow rate of the compound present in the polymer production apparatus 10, a power amount of at least one control unit included in the production device, a temperature of the production device, and a pressure within the production device, but is not limited thereto.

According to an example, the process information corresponding to the second time point includes the information on input raw materials input to the polymer production apparatus 10 during a preset time period from the second time point, the information on the amount of polymer produced (polymer production information) by the polymer production apparatus 10 during the preset time period from the second time point, and information on the process status of the polymer production apparatus 10 at the second time point.

According to an embodiment, the processor 130 may identify predicted process information corresponding to a third time point when the preset time elapses from the second time point based on the process history information and the process information corresponding to the second time point.

The process history information refers to the history information on the process before the second time point performed in the polymer production apparatus 10, and according to an example, may include the history information before the second time point on the amount of input raw materials input to the polymer production apparatus 10 (not illustrated), the amount of polymer produced in the polymer production apparatus 10 (not illustrated), and the process status of the polymer production apparatus 10 (not illustrated). The predicted process information refers to process information at a third time point predicted based on the process history information and the process information corresponding to the second time point. This will be described in detail with reference to FIG. 4.

According to an embodiment, the processor 130 may input the received process information corresponding to the second time point and the identified predicted process information corresponding to the third time point to the trained neural network model to acquire the predicted quality information of the polymer corresponding to the third time point. Here, the quality information refers to information on the quality of the produced polymer acquired from the polymer production apparatus 10. According to an example, the quality information may include at least one of information on a MI value, a density value, or an MFR value of the produced polymer.

According to an example, when the process information corresponding to the second time point and the predicted process information corresponding to the third time point are input, the trained neural network model may acquire the predicted quality information of the polymer corresponding to the third time point. Here, the predicted quality information may include at least one of the information on the MI value, the density value, or the MFR value of the polymer produced by the polymer production apparatus 10 at the third time point when the preset time elapses from the second time point.

According to an embodiment, the processor 130 may provide guide information including the acquired predicted quality information. According to an example, the guide information may be information that guides the predicted quality to be equal to or greater than a preset value when the predicted quality at the third time point is less than the preset value based on the predicted quality information, but is not limited thereto. The method of providing guide information will be described in detail through FIGS. 6 to 9.

Figure 3:
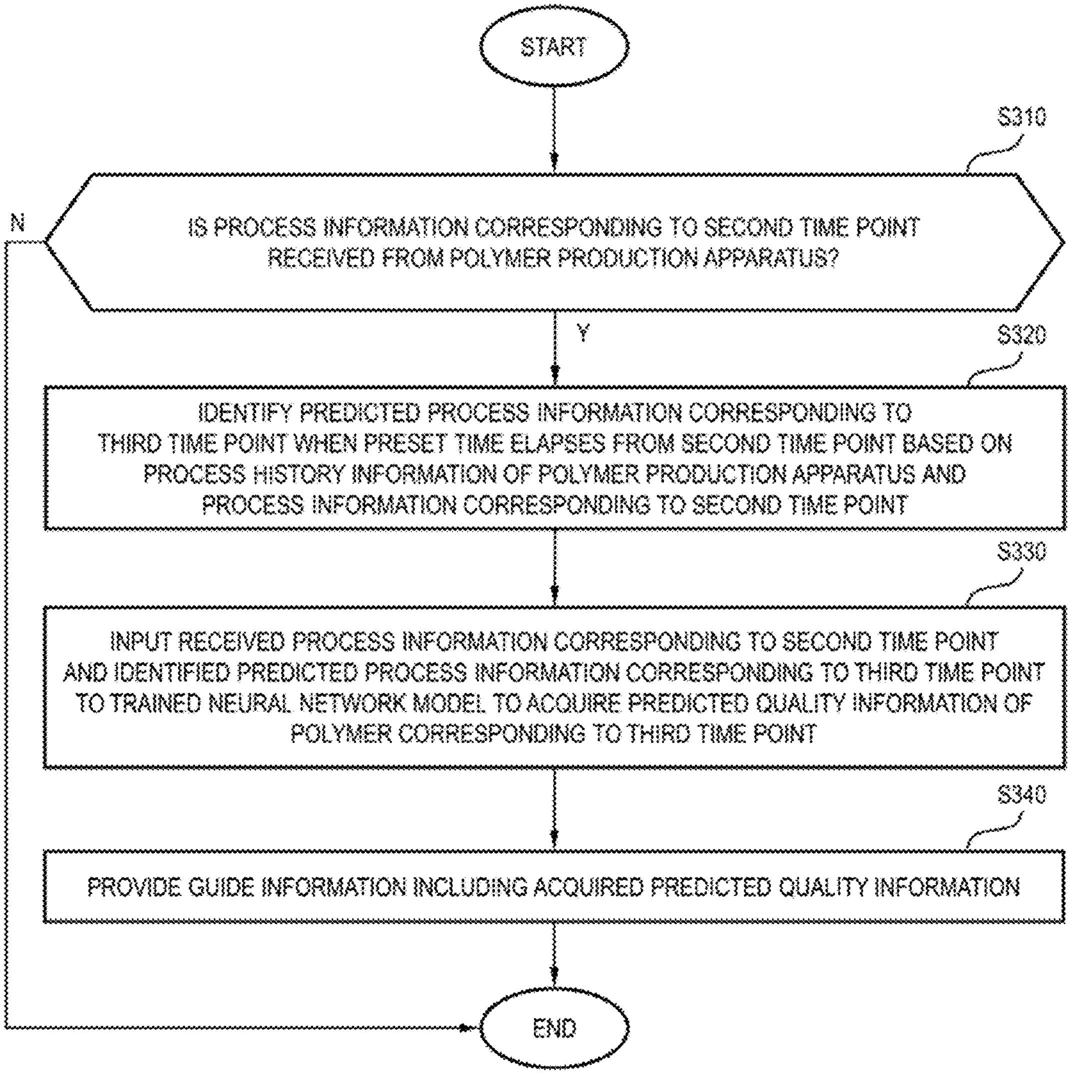
FIG. 3 is a flowchart for describing the control method of an electronic device according to the embodiment of the present disclosure.

FIG. 3 is a flowchart for describing a control method of an electronic device according to an embodiment of the present disclosure.

Referring to FIG. 3, according to an embodiment, the control method may identify whether the process information corresponding to the second time point is received from the polymer production apparatus (S310). According to an example, the processor 130 may receive the process information corresponding to the second time point of the polymer production apparatus 10 from at least one of an external device (not illustrated), for example, the polymer production apparatus 10, or an external server (not illustrated) through the communication interface 110.

Subsequently, according to an embodiment, when the process information is received (Y), the control method may identify the predicted process information corresponding to the third time point when the preset time elapses from the second time point based on the process history information of the polymer production apparatus 10 and the process information corresponding to the second time point (S320).

According to an example, the processor 130 may acquire the process information including the input raw material information and the polymer production information corresponding to each of a plurality of time points before the second time point based on the process history information. Subsequently, according to an example, the processor 130 may use a statistical analysis application stored in the memory 120 to acquire relationship information between the input raw material information and the polymer production information. Here, the relationship information may be a formula corresponding to the relationship between the input raw material information and the polymer production information acquired using a regression analysis model. Subsequently, the processor 130 may acquire predicted polymer production information at the third time point according to the input raw materials at the second time point based on the acquired relationship information.

However, the processor 130 is not limited thereto, and it may use a statistical analysis application to acquire relationship information among the input raw materials, the process status, and the polymer production information and acquire the predicted polymer production information at the third point in time based on the relationship information.

Alternatively, according to an example, the processor 130 may acquire the predicted input raw material information, the predicted process status information, and the predicted polymer production information corresponding to the third time point based on the process history information. For example, the processor 130 may use a statistical analysis application to acquire trend information on each of the input raw material information, the process status information, and the polymer production information. Here, the trend information may be a formula acquired using a regression analysis model. The processor 130 may acquire the predicted input raw material information, the prediction process status information, or the predicted polymer production information corresponding to the third time point based on the acquired trend information and the process information corresponding to the second time point.

Subsequently, according to an embodiment, in the control method, the received process information corresponding to the second time point and the identified predicted process information corresponding to the third time point may be input to the trained neural network model to acquire the predicted quality information of the polymer corresponding to the third time point (S330).

According to an example, the processor 130 may input the input raw material information at the second time point, the process status information at the second time point, and the acquired predicted polymer production information at the third time point to the trained neural network model to acquire the predicted quality information on the produced polymer at the third time point.

Subsequently, according to an embodiment, the control method may provide the guide information including the acquired predicted quality information (S340). According to an example, the electronic device 100 may further include a display (not illustrated), and the processor 130 may display a UI including the guide information through the display.

According to the above-described example, a preprocessing process is performed on the acquired process information, and the preprocessed process information may be input to the trained neural network model to acquire the predicted process information. Accordingly, it is possible to accurately predict the quality of the polymer acquired through the polymer production process and provide the guide information to the user based on the predicted quality.

Figure 4:
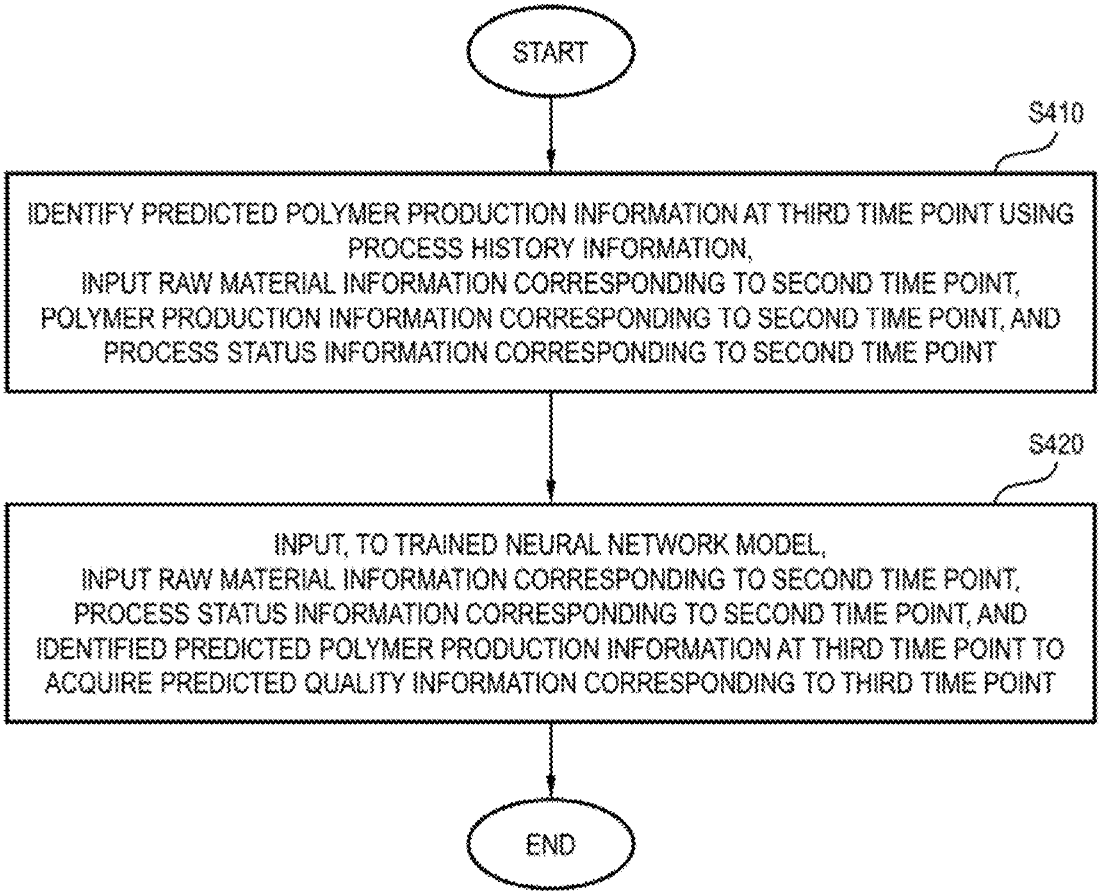
FIG. 4 is a diagram for describing a method of acquiring predicted quality information according to an embodiment.

FIG. 4 is a diagram for describing a method of acquiring predicted quality information according to an embodiment.

Referring to FIG. 4, according to an embodiment, the control method may use the process history information, the input raw material information corresponding to the second time point, the polymer production information corresponding to the second time point, and the process status information corresponding to the second time point to identify the predicted polymer production information at the third time point (S410).

According to an example, the processor 130 may first acquire the process information including the input raw material information and the polymer production information corresponding to each of a plurality of time points before the second time point based on the process history information stored in the memory 120. Subsequently, according to an example, the processor 130 may use a statistical analysis application stored in the memory 120 to acquire the relationship information among the input raw material information, the production status information, and the polymer production information. Here, the relationship information may be a formula acquired using a regression analysis model. Subsequently, the processor 130 may acquire predicted polymer production information at the third time point according to the input raw materials at the second time point based on the acquired relationship information.

For example, the processor 130 may input the input raw material information and the production status information at the second time point to the formula included in the acquired relationship information to acquire the predicted polymer production information at the third time point.

Subsequently, according to an embodiment, in the control method, the input raw material information corresponding to the second time point, the process status information corresponding to the second time point, and the identified predicted polymer production information at the third time point may be input to the trained neural network model to acquire the predicted quality information corresponding to the third time point (S420).

Here, the neural network model may be a neural network model that is trained to output the predicted quality information when the process information including the input raw material information, the polymer production information, the process status information, and the predicted polymer production information are input. According to an example, since a data set including input raw material information at an nth time point, process status information at the nth time point, and accordingly, polymer production information at an n+1 time point is input to the neural network model as training data, the neural network model may be trained. In this case, the data set may include a label corresponding to the quality information of the polymer produced at the n+1 time point.

Meanwhile, the artificial neural network (or neural network model) according to an embodiment of the present disclosure may include a DNN, and examples of the artificial neural network may include a CNN, a DNN, a RNN, an RBM, a DBN, a BRDNN, a deep Q-Network, and the like, but are not limited thereto.

However, the trained neural network model is not limited to the above, and according to an example, the trained neural network model may be a trained neural network model that outputs the predicted quality information when the process information including the input raw material information, the polymer production information, and the process status information is input. That is, even when the predicted polymer production information is not input, the predicted quality information may be output by receiving the process information including the input raw material information, the polymer production information, and the process status information to output the predicted quality information.

Meanwhile, according to an embodiment, the processor 130 may train the neural network model using process history information. According to an example, the processor 130 may parse the process information and quality information corresponding to each of a plurality of time points before the second time point included in the process history information to acquire the data set for training the neural network model, and train the neural network model using the acquired data set as training data. In this case, the label of each data set may be quality information of the produced polymer.

Figure 5:
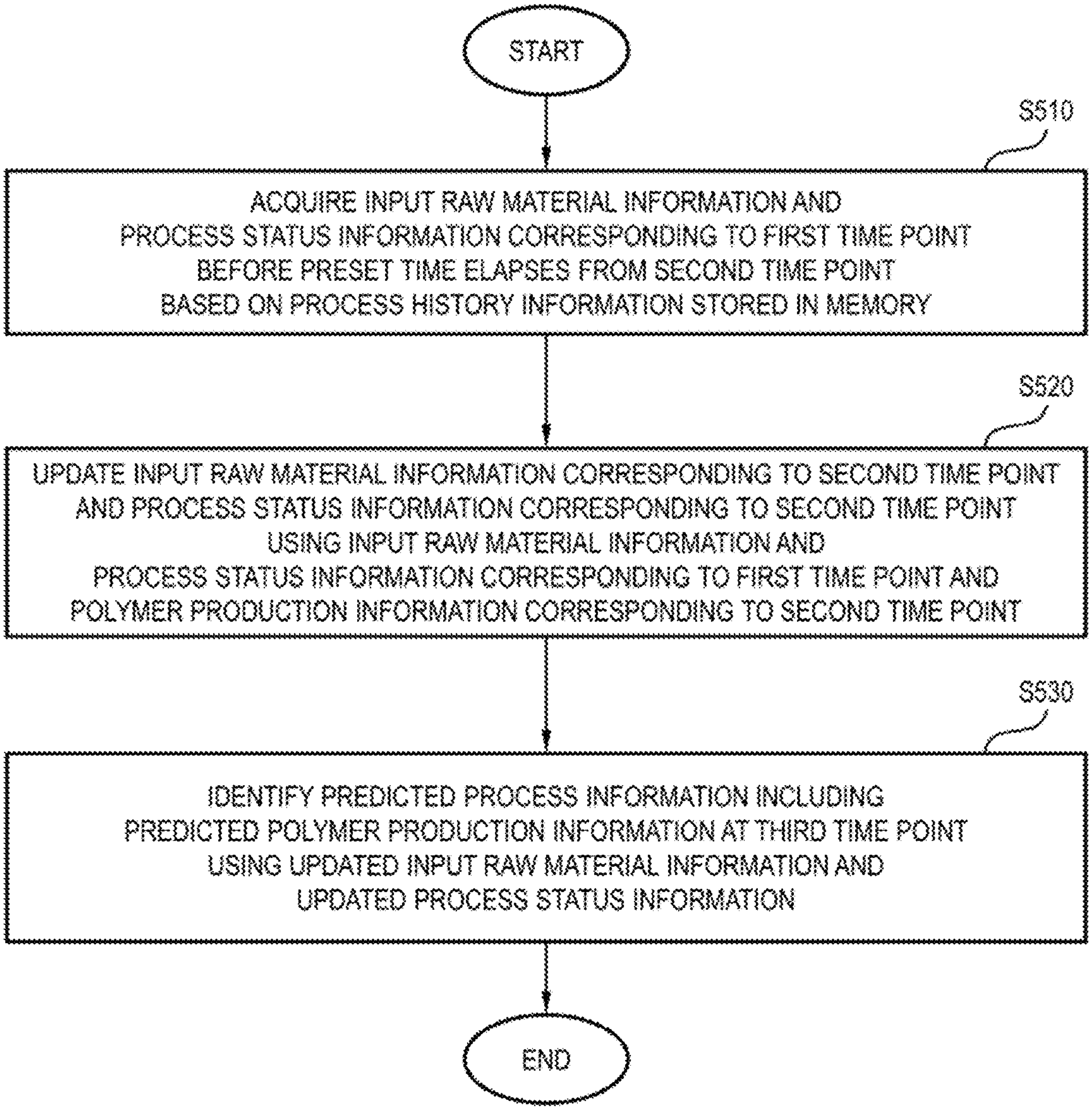
FIG. 5 is a diagram for describing a method of identifying predicted process information according to an embodiment.

FIG. 5 is a diagram for describing a method of identifying predicted process information according to an embodiment.

According to an embodiment, in the control method, the input raw material information and the process status information corresponding to the first time point before a preset time elapses from the second time point may first be acquired based on the process history information stored in the memory 120 (S510). That is, it may become a second time point when a preset time elapses from the first time point, and it may become a third time point when a preset time elapses from the second time point. However, the embodiment is not limited thereto.

Subsequently, according to an embodiment, in the control method, the input raw material information and the process status information corresponding to the first time point and the polymer production information corresponding to the second time point may be used to update the input raw material information corresponding to the second time point and the process status information corresponding to the second time point (S520).

According to an example, the processor 130 may acquire the input raw material information and the process status information reflecting the accumulated process before the second time point based on the input raw material information, the process status information, and the polymer production information corresponding to each of a plurality of time points included in the process history information.

For example, assuming that the input raw material corresponding to the nth time point is 1 and that there is no disturbance, the case of a process in which the amount of produced polymer is 2 at an $n+1^{th}$ time point according to the input raw material at the nth time point is assumed (here, n is an integer). When it is identified based on the process history information that the input raw material corresponding to the first time point is 1 and the amount of produced polymer corresponding to the second time point is 1.8 (i.e., when only 90% of the input raw material is produced as a polymer), the processor may identify that the amount of recovered raw materials is 10% of the total input amount, and thus, update the amount of input raw materials at the second time point to 1.1. Subsequently, when the updated input raw material information and process status information at the second time point are identified, the processor 130 may use the acquired relationship information to identify the predicted polymer production information at the third time point.

However, the present disclosure is not limited to the above, and the updated value of the input raw material corresponding to the first time point may be identified according to the process corresponding to each of the plurality of time points before the first time point, and thus, the amount of input raw materials and the process status information at the second time point may be updated to different values.

Subsequently, according to an embodiment, in the control method, the updated input raw material information and the updated process status information may be used to identify the predicted process information including the predicted polymer production information at the third time point (S530).

According to an example, the processor 130 may use the process information acquired based on the updated process information and process history information including the input raw material information and the process status information at the second time point to identify the predicted process information including the predicted polymer production information at the third time point.

According to the above-described example, by updating the data to be input to the trained neural network model by reflecting the accumulated process history information and inputting the updated data to the trained neural network model, it is possible to more accurately predict quality.

Figure 6:
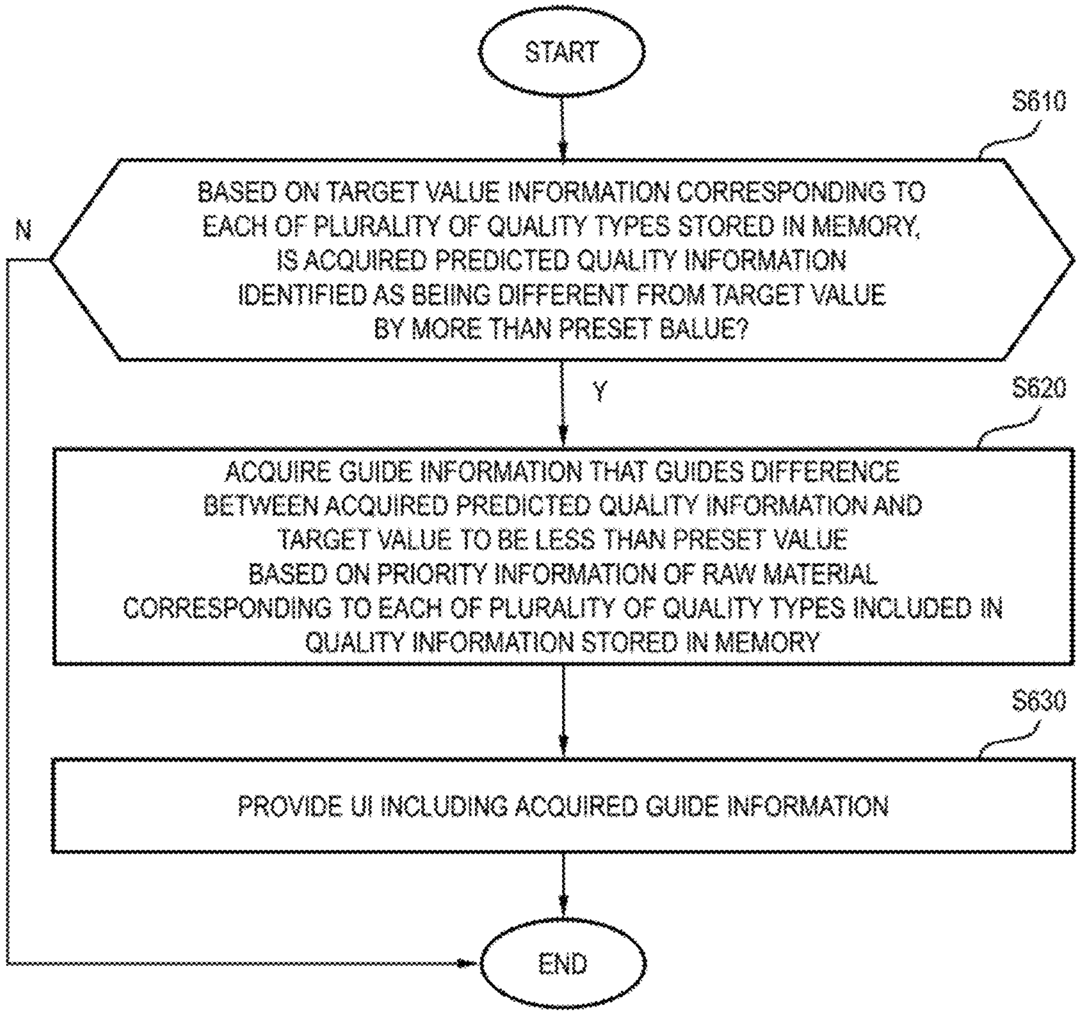
FIG. 6 is a diagram for describing a method of acquiring guide information according to an embodiment.

FIG. 6 is a diagram for describing a method of acquiring guide information according to the embodiment.

Referring to FIG. 6, according to an embodiment, in the control method, based on the target value information corresponding to each of the plurality of quality types stored in the memory 120, whether the acquired predicted quality information differs from a target value by more than a preset value may be identified (S610).

According to an example, the memory 120 may store information on the target value corresponding to each of the plurality of quality types. The processor 130 may compare the predicted quality information acquired through the neural network model with the target value stored in the memory 120 to identify whether the acquired predicted quality information differs from the target value by more than the preset value. For example, by comparing at least one of the information on the MI value, the density value, or the MFR value of the produced polymer included in the predicted quality information with the corresponding value among the MI target value, the density target value, or the MFR target value stored in the memory 120, it is possible to identify whether the acquired predicted quality information differs from the target value by more than the preset value.

Subsequently, the processor 130 may acquire the guide information that guides the difference between the acquired predicted quality information and the target value to be less than the preset value based on the priority information of the raw materials corresponding to each of the plurality of quality types included in the quality information stored in the memory 120 (S620).

According to an example, the memory 120 may store the priority information of the raw materials corresponding to each quality type. For example, the highest priority corresponding to the MI may be a catalyst, and the highest priority corresponding to the density may be the ratio of butene to ethylene.

According to an example, when the predicted MI value differs from the target value by more than the preset value, the processor 130 may identify the amount of catalyst for making the MI value differs from the target value by less than the preset value and acquire guide information including the information on the identified amount of catalyst.

In this case, according to an example, the memory 120 may pre-store the information on the change value in quality according to the change in unit input amount corresponding to each of the plurality of raw material types, and the processor 130 may identify the guide information for making the predicted quality value differs form the target value by less that the preset value based on the information stored in the memory 120.

However, the present disclosure is not limited to the above, and the processor 130 may acquire guide information corresponding to each of the plurality of types of predicted quality information using the trained neural network model. This will be described in detail with reference to FIG. 7.

Subsequently, according to an embodiment, in the control method, a UI including the acquired guide information may be provided (S630). According to an example, the UI may include process information corresponding to the second time point, the process history information, and the predicted quality information of the polymer corresponding to the third time point.

Meanwhile, according to an embodiment, the processor 130 may further include a user interface (not illustrated), and when a user input corresponding to the acquired guide information is received through the user interface (not illustrated), the processor 130 may identify control information corresponding to the received user input and transmit the identified control information to the control engine through the communication interface 110. Here, the control engine refers to an engine that controls the polymer production apparatus 10.

According to an example, after a UI including guide information is provided, when the user input for lowering the catalyst input amount to the preset value is received through the user interface, the processor 130 may identify control information for lowering the catalyst input amount to the preset value and transmit the identified control information to the control engine through the communication interface 110.

Figure 7:
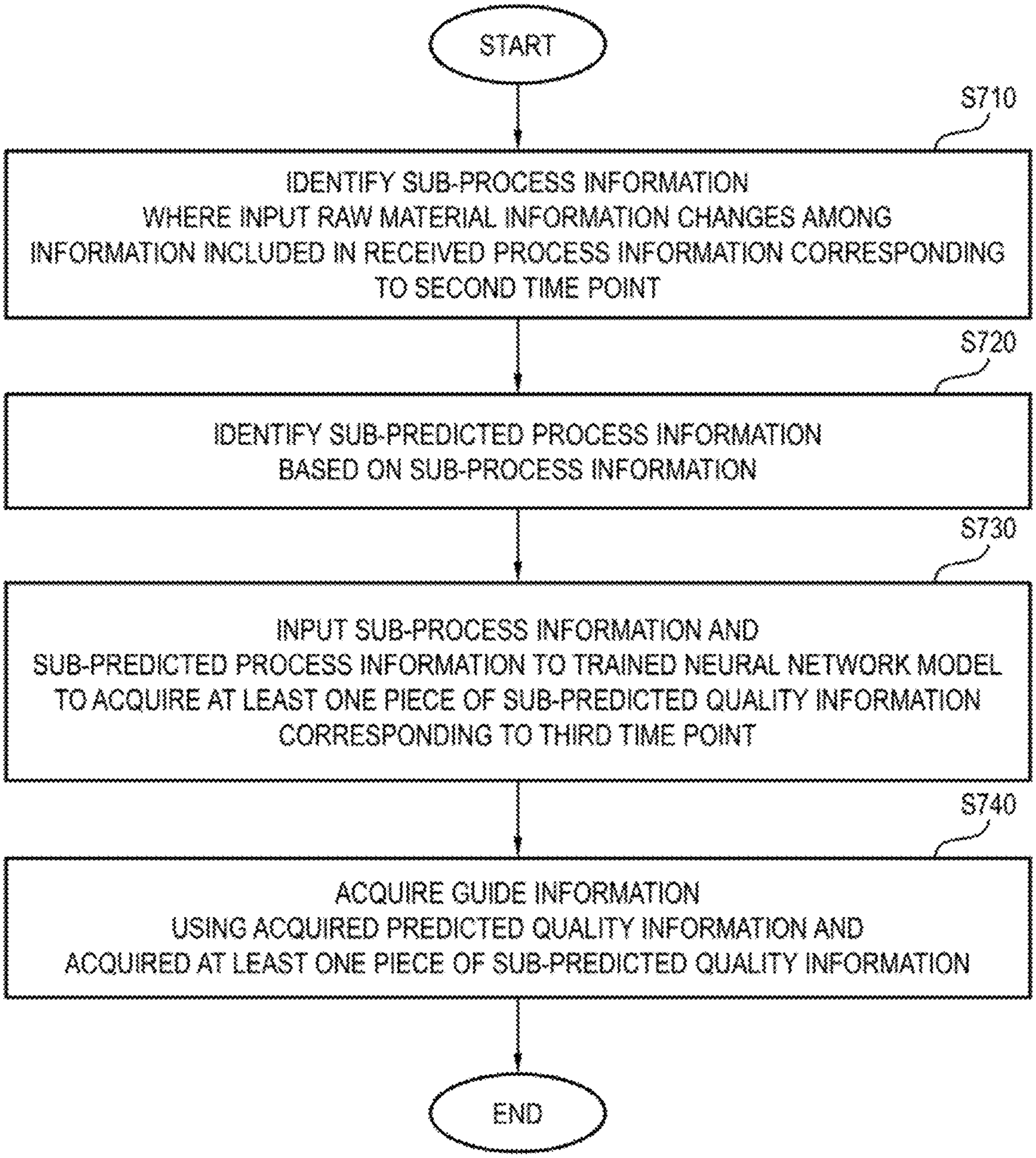
FIG. 7 is a diagram for describing a method of acquiring guide information according to an embodiment.

FIG. 7 is a diagram for describing a method of acquiring guide information according to the embodiment.

According to an embodiment, in the control method, sub-process information in which the input raw material information changes among the information included in the received process information corresponding to the second time point may first be identified (S710). Here, the sub-process information may be process information in which the ratio of input raw materials changes by a preset value, but is not limited thereto, and according to an example, the sub-process information may be process information in which the process status (e.g., pressure level in the polymer production apparatus 10) changes.

Subsequently, according to an embodiment, in the control method, sub-predicted process information may be identified based on the sub-process information (S720).

Subsequently, according to an embodiment, the control method may input the sub-process information and the sub-predicted process information to the trained neural network model to acquire at least one piece of sub-predicted quality information corresponding to the third time point (S730).

Subsequently, according to an embodiment, the control method may acquire guide information using the acquired predicted quality information and at least one piece of acquired sub-predicted quality information (S740).

According to an example, the processor 130 may compare the acquired predicted quality information and sub-predicted quality information to acquire guide information. For example, the processor 130 may compare the acquired sub-predicted quality information and predicted quality information to acquire the information on the amount of change in the MI value as the unit input amount of catalyst changes.

However, the present disclosure is not limited the above, and the processor 130 may acquire guidance information through the predicted quality information and sub-predicted quality information acquired using a preset algorithm. The processor 130 may obtain guide information including the acquired guidance information.

Figure 8:
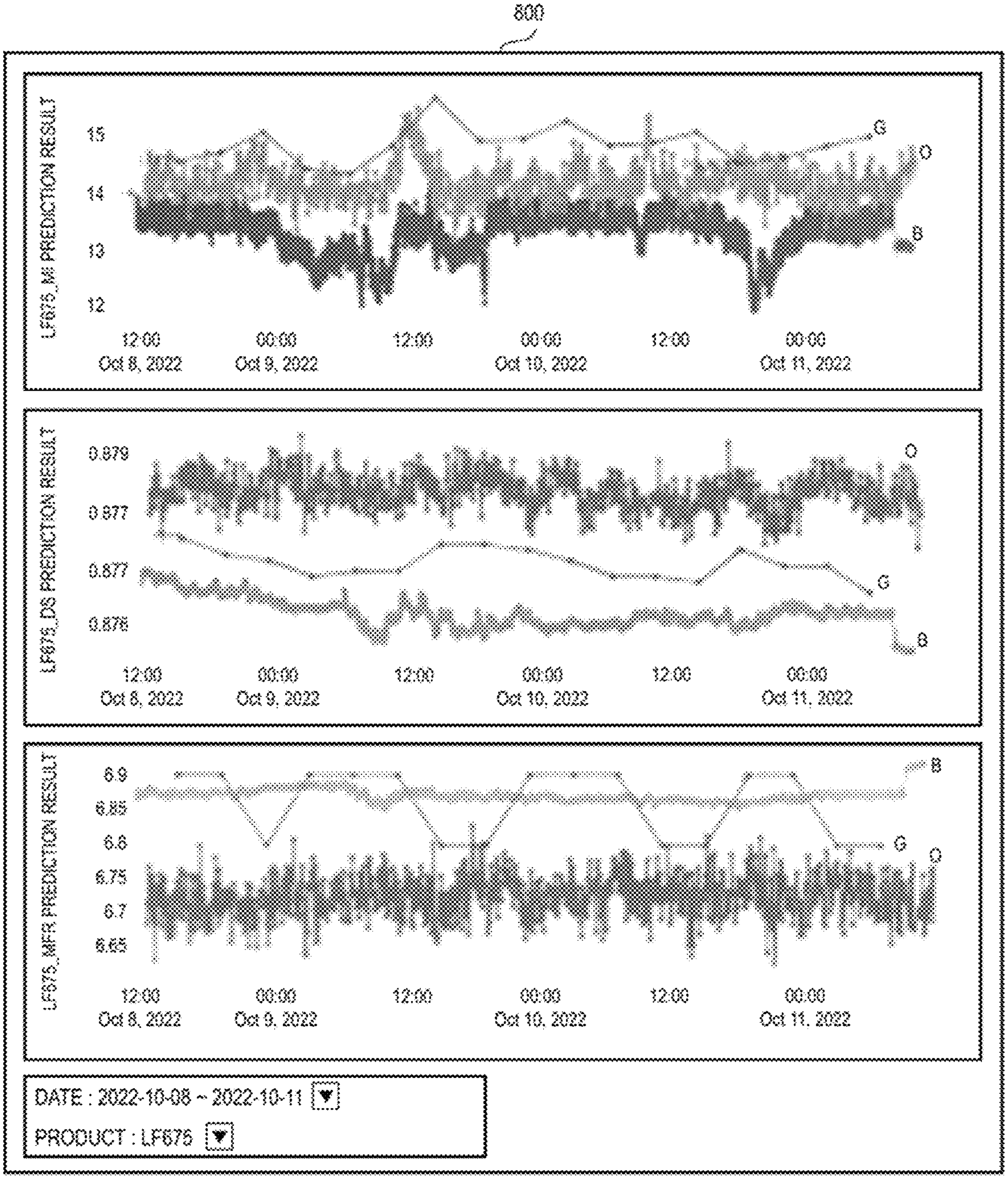
FIG. 8 is a diagram for describing a method of providing a user interface (UI) according to an embodiment.

FIG. 8 is a diagram for describing a method of providing a user interface (UI) according to an embodiment.

Referring to FIG. 8, according to an embodiment, the processor 130 may provide a UI 800 including process history information. According to an example, the processor 130 may provide the UI 800 including information in which the input raw material information (for example, input amount corresponding to each of the plurality of types of raw materials), the process status information, and the polymer production information corresponding to each of a plurality of time points before the second time point are implemented in a graph form.

In this case, according to an example, the electronic device 100 may further include a display (not illustrated), and the processor 130 may display the UI through the display.

Figure 9:
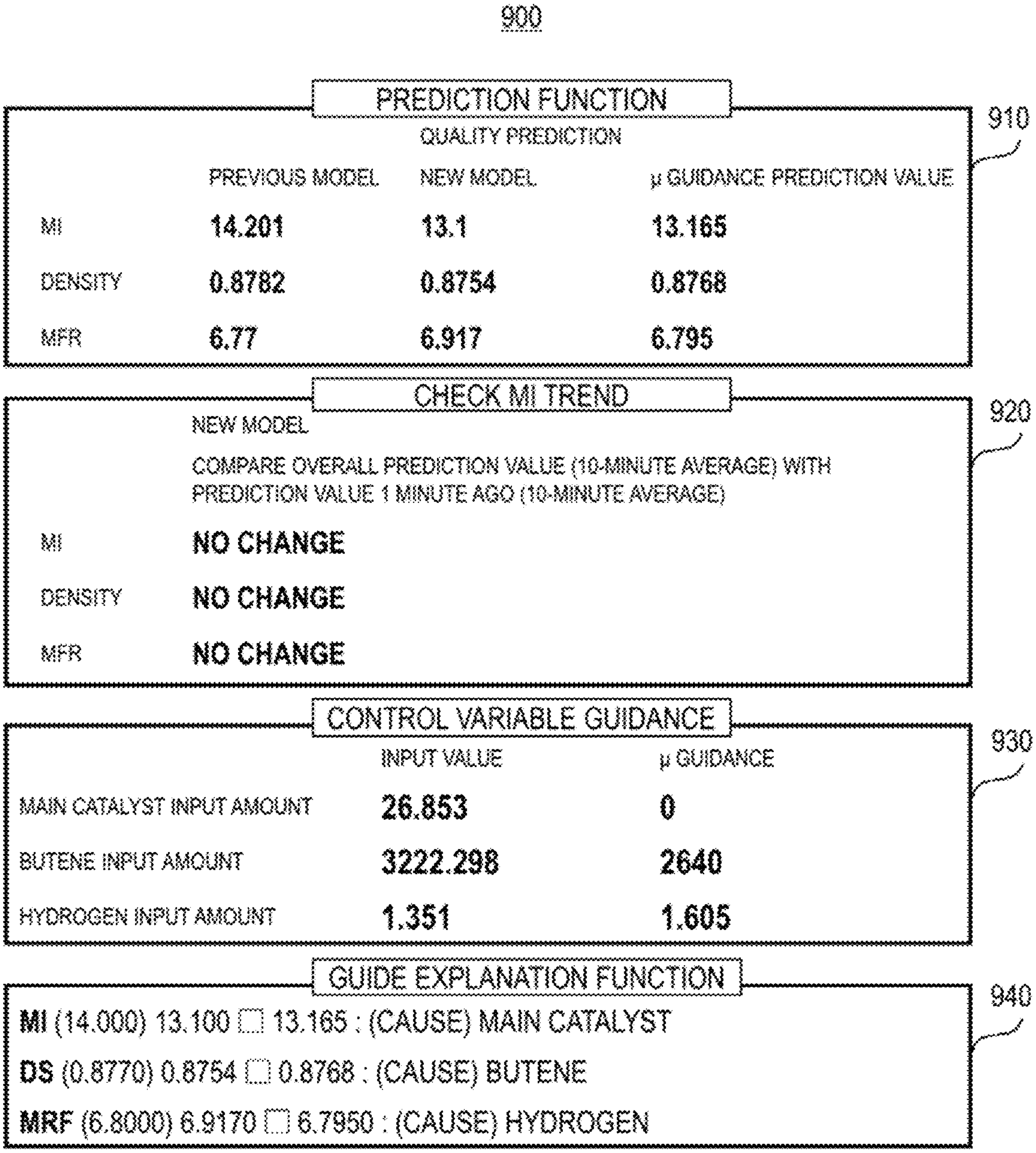
FIG. 9 is a diagram for describing a method of providing a UI according to an embodiment.

FIG. 9 is a diagram for describing a method of providing a UI according to an embodiment.

Referring to FIG. 9, according to an embodiment, the processor 130 may provide a UI 900 including guide information that includes predicted quality information 910 corresponding to the third time point, trend information 920 corresponding to each of the plurality of types of quality, guidance information 930 for control variables, and explanatory function information 940 corresponding to each of the plurality of qualities.

Here, the predicted quality information 910 may include predicted quality information when the current input amount is completed with the produced polymer and previous quality information. The trend information 920 may include history information for each of a plurality of qualities. The processor 130 may acquire the history information for each of the plurality of qualities based on process history information. The control variable guidance information 930 may include information on an input amount corresponding to each of a plurality of types of control variables and guidance information corresponding to each of a plurality of types of quality information predicted using the trained neural network model. Alternatively, according to an example, guidance information corresponding to each of a plurality of types of quality information stored in the memory 120 may be included. The explanatory function information 940 may include information on the target value corresponding to each of the plurality of qualities and the amount of change in the quality value as the unit input amount of each of the plurality of qualities changes. In this case, information on the highest priority control variable corresponding to each of the plurality of qualities may be included.

Figure 10:
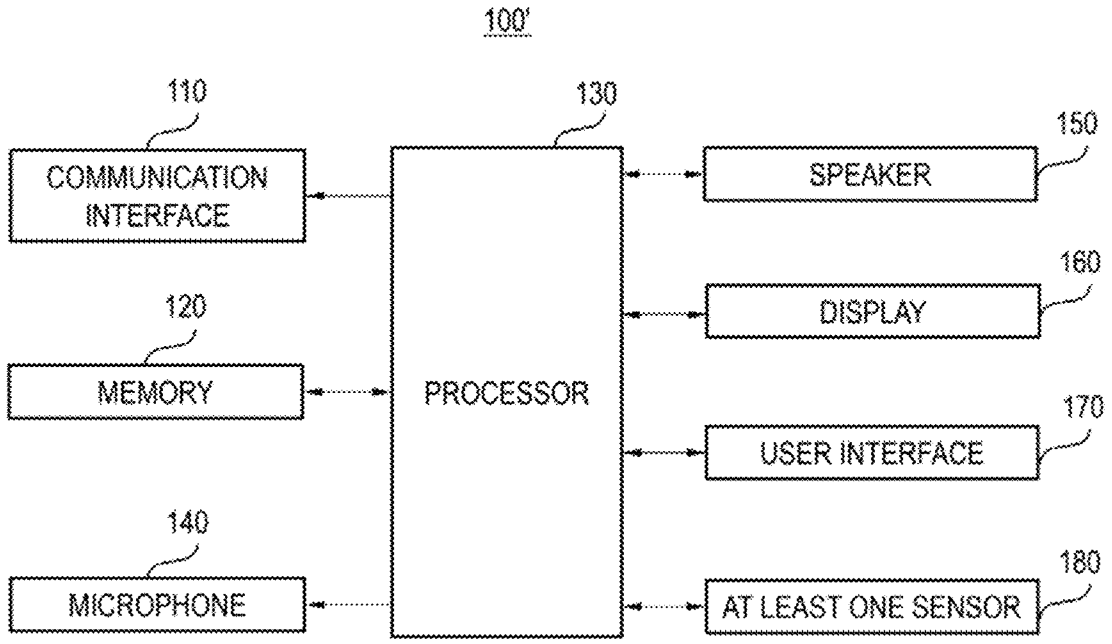
FIG. 10 is a block diagram illustrating a detailed configuration of an electronic device according to an embodiment.

FIG. 10 is a block diagram illustrating a detailed configuration of an electronic device according to an embodiment.

Referring to FIG. 10, an electronic device 100' includes a communication interface 110, a memory 120, one or more processors 130, a microphone 140, a speaker 150, a display 160, a UI 170, and at least one sensor 180. Detailed descriptions of components overlapping with components illustrated in FIG. 2 among components illustrated in FIG. 10 will be omitted.

The microphone 140 may refer to a module that acquires sound and converts the acquired sound into an electrical signal and may be a condenser microphone, a ribbon microphone, a moving coil microphone, a piezoelectric element microphone, a carbon microphone, or a micro electro mechanical system (MEMS) microphone. In addition, it may be implemented in a non-directional, bi-directional, unidirectional, sub-cardioid, super-cardioid, or hyper-cardioid manner.

There may be various embodiments in which the electronic device 100' performs an operation corresponding to a user voice signal received through the microphone 140.

As an example, the electronic device 100' may control the display 160 based on the user voice signal received through the microphone 140. For example, when a user voice signal for displaying content A is received, the electronic device 100' may control the display 160 to display content A.

As another example, the electronic device 100' may control an external display device connected to the electronic device 100' based on a user voice signal received through the microphone 140. Specifically, the electronic device 100' may provide a control signal for controlling the external display device so that an operation corresponding to the user voice signal is performed on the external display device and may transmit the provided control signal to the external display device. Here, the electronic device 100' may store a remote control application for controlling an external display device. In addition, the electronic device 100' may transmit the provided control signal to the external display device using at least one communication method among Bluetooth, Wi-Fi, or infrared rays. For example, when a user voice signal for displaying content A is received, the electronic device 100' may transmit a control signal for controlling the content A to be displayed on the external display device to the external display device. Here, the electronic device 100' may refer to various terminal devices capable of installing remote control applications such as a smart phone and an AI speaker.

As another example, the electronic device 100' may use a remote control device to control the external display device connected to the electronic device 100' based on the user voice signal received through the microphone 140. Specifically, the electronic device 100' may provide, to the remote control device, a control signal for controlling the external display device so that an operation corresponding to the user voice signal is performed on the external display device. The remote control device may transmit the control signal received from the electronic device 100' to the external display device. For example, when a user voice signal for displaying the content A is received, the electronic device 100' may transmit the control signal for controlling the content A to be displayed on the external display device to the external display device, and the remote control device may transmit the received control signal to the external display device.

The speaker 150 may include a tweeter for high-pitched sound reproduction, a mid-range woofer for mid-range sound reproduction, a woofer for low-pitched sound reproduction, a subwoofer for extremely low-pitched sound reproduction, an enclosure for controlling resonance, a crossover network that divides an electric signal frequency input to the speaker by bands, etc.

The speaker 150 may output a sound signal to the outside of the electronic device 100'. The speaker 150 may output multimedia reproduction, recording reproduction, various kinds of notification sounds, voice messages, and the like. The electronic device 100' may include an audio output device such as the speaker 150, or may include an output device such as an audio output terminal. In particular, the speaker 150 may provide acquired information, information processed/produced based on the acquired information, a response result or an operation result to a user's voice, or the like in the form of voice.

The display 160 may be implemented by a display including a self-light emitting element or a display including a non-light emitting element and a backlight. For example, the display 160 may be implemented by various types of displays such as a liquid crystal display (LCD), an organic light emitting diode (OLED) display, a light emitting diode (LED), a micro LED, a mini LED, a plasma display panel (PD), a quantum dot (QD) display, and a quantum dot light-emitting diode (QLED). A driving circuit, a backlight unit, and the like, and the like, may be included in the display 160, and the driving circuit may be implemented in a form such as an a-Si TFT, low temperature poly silicon (LTPS) TFT, an organic TFT (OTFT). Meanwhile, the display 160 may be implemented by a touch screen combined with a touch sensor, a flexible display, a rollable display, a 3D display, a display to which a plurality of display modules are physically connected, and the like. The processor 130 may control the display 160 to output the output image acquired according to various embodiments described above. Here, the output image may be a high-resolution image of 4K or 8K or higher.

Meanwhile, according to another embodiment, the electronic device 100' may not include the display 160. The electronic device 100' may be connected to an external display device and may transmit an image or content stored in the electronic device 100' to the external display device. Specifically, the electronic device 100' may transmit an image or content to an external display device along with a control signal for controlling the image or content to be displayed on the external display device.

Here, the external display device may be connected to the electronic device 100' through the communication interface 110 or an input/output interface (not illustrated). For example, the electronic device 100' may not include a display like a set top box (STB). Also, the electronic device 100' may include only a small display capable of displaying only simple information such as text information. Here, the electronic device 100' may transmit an image or content to an external display device wired or wirelessly through the communication interface 110 or transmit an image or content to an external display device through an input/output interface (not illustrated).

The UI 170 is a configuration that allows the electronic device 100' to interact with a user. For example, the UI 170 may include at least one of a touch sensor, a motion sensor, a button, a jog dial, a switch, a microphone, or a speaker, but is not limited thereto.

At least one sensor 180 (hereinafter referred to as a sensor) may include various types of sensors. The sensor 180 may measure a physical quantity or detect an operating state of the electronic device 100' and convert the measured or detected information into an electrical signal. The sensor 180 may include a camera, and the camera may include a lens for focusing visible light and other optical signals received after being reflected by an object into an image sensor, and an image sensor capable of detecting visible light and other optical signals. Here, the image sensor may include a 2D pixel array divided into a plurality of pixels.

According to the above-described example, a preprocessing process is performed on the acquired process information, and the preprocessed process information may be input to a trained neural network model to acquire predicted process information. Accordingly, it is possible to accurately predict the quality of the polymer acquired through the polymer production process and provide guide information to the user based on the predicted quality.

Meanwhile, the above-described methods according to various embodiments of the present disclosure may be implemented in a form of application that may be installed on existing electronic devices. Alternatively, the above-described methods according to various embodiments of the present disclosure may be performed using a deep learning-based learned neural network (or deep learned neural network), that is, a learning network model. In addition, the above-described methods according to various embodiments of the present disclosure may be implemented only by upgrading the software or hardware of an existing electronic device. In addition, various embodiments of the present disclosure described above can be performed through an embedded server provided in the electronic device or a server outside the electronic device.

Meanwhile, according to an embodiment of the disclosure, the various embodiments described above may be implemented by software including instructions stored in a machine-readable storage medium (for example, a computer-readable storage medium). A machine may be a device that invokes the stored instruction from the storage medium and may be operated depending on the invoked instruction, and may include a display device (for example, display device A) according to the disclosed embodiments. In the case in which an instruction is executed by the processor, the processor may directly perform a function corresponding to the instruction or other components may perform the function corresponding to the instruction under a control of the processor. The instruction may include code provided or executed by the compiler or an interpreter. The machine-readable storage medium may be provided in the form of a non-transitory storage medium. Here, the term "non-transitory" means that the storage medium is tangible without including a signal and does not distinguish whether data is semi-permanently or temporarily stored in the storage medium.

In addition, according to an embodiment, the above-described methods according to the various embodiments may be included and provided in a computer program product. The computer program product may be traded as a product between a seller and a purchaser. The computer program product may be distributed in the form of a storage medium (for example, a compact disc read only memory (CD-ROM)) that may be read by the machine or online through an application store (for example, Play Store™). In case of online distribution, at least a portion of the computer program product may be at least temporarily stored in a storage medium such as a memory of a server of a manufacturer, a server of an application store, or a relay server or be temporarily provided.

In addition, each of the components (for example, modules or programs) according to various embodiments described above may include a single entity or a plurality of entities, and some of the corresponding sub-components described above may be omitted or other sub-components may be further included in the various embodiments. Alternatively or additionally, some components (e.g., modules or programs) may be integrated into one entity and perform the same or similar functions performed by each corresponding component prior to integration. Operations performed by the modules, the programs, or the other components according to the various embodiments may be executed sequentially, in parallel, iteratively, or heuristically, at least some of the operations may be performed in a different order or are omitted, or other operations may be added.

Although exemplary embodiments of the present disclosure have been illustrated and described hereinabove, the present disclosure is not limited to the above-described specific exemplary embodiments, but may be variously modified by those skilled in the art to which the present disclosure pertains without departing from the gist of the present disclosure as disclosed in the accompanying claims. These modifications should also be understood to fall within the scope and spirit of the present disclosure.

INDUSTRIAL APPLICABILITY

The electronic device for implementing a polymer quality prediction and control system and a control method thereof as described above can be applied to the polymer production process field.

The invention claimed is:

1. An electronic device for implementing a quality prediction and control system, comprising:

a communication interface;

a memory that stores a trained neural network model and process history information of a polymer production apparatus, the process history information including input raw material information, polymer production information, process status information, and quality information on the produced polymer corresponding to a first time point, and stores priority information of raw materials corresponding to each of a plurality of types of quality information included in the quality information and target value information corresponding to each of the plurality of types of quality information, the plurality of types of quality information including at least one of a melting index (MI) value, a density value, and a melt flow index (MFR) value of the produced polymer; and one or more processors that acquire the input raw material information corresponding to the first time point before a preset time elapses from a second time point and process status information corresponding to the first time point based on the process history information, when process information including input raw material information, polymer production information, and process status information corresponding to the second time point is received from the polymer production apparatus through the communication interface, use the input raw material information corresponding to the first time point, the process status information corresponding to the first time point, and the polymer production information corresponding to the second time point to update the input raw material information corresponding to the second time point and the process status information corresponding to the second time point, the updating of the input raw material information corresponding to the second time point is reflecting an amount of recovered raw materials among an amount of input raw materials at the first time point in an amount of input raw materials at the second time point, use the updated input raw material information and the updated process status information to identify predicted process information including predicted polymer production information at a third time point when a preset time elapses from the second time point, input the updated input raw material information, the updated process status information, and the predicted polymer production information at the third time point to the trained neural network model to acquire predicted quality information of the polymer corresponding to the third time point, acquire guide information that guides a difference between the acquired predicted quality information and the target value to be less than a preset value based on priority information of raw materials, when the acquired predicted quality information differs from the target value by more than a preset value, and provide a user interface (UI) including the acquired guide information, wherein the UI includes at least one of the process history information, the predicted quality information of the polymer corresponding to the third time point, trend information corresponding to each of the plurality of types of quality information, explanatory function information corresponding to each of the plurality of types of quality information, and control variable guidance information corresponding to each of the plurality of types of quality information.

2. The electronic device of claim 1, wherein the process history information includes input raw material information, polymer production information, process status information, and quality information of the produced polymer corresponding to each of a plurality of time points before the second time point, and the trained neural network model is trained to output the predicted quality information when the process information including the input raw material information, the polymer production information, and the process status information and the predicted polymer production information are input.

3. The electronic device of claim 1, wherein the UI further includes process information corresponding to the second time point.

4. The electronic device of claim 3, wherein the one or more processors identify sub-process information in which the input raw material information changes among the information included in the received process information corresponding to the second time point, identify sub-predicted process information based on the sub-process information, input the sub-process information and the sub-predicted process information to the trained neural network model to acquire at least one piece of sub-predicted quality information corresponding to the third time point, and use the acquired predicted quality information and the acquired at least one piece of sub-predicted quality information to acquire the guide information.

5. The electronic device of claim 3, further comprising a UI, wherein, when a user input corresponding to the acquired guide information is received through the UI, the one or more processors identify control information corresponding to the received user input, and transmit the identified control information to a control engine through the communication interface.

6. A control method of an electronic device for implementing a quality prediction and control system, the control method comprising:

storing, in a memory, process history information of a polymer production apparatus, the process history information including input raw material information, polymer production information, process status information, and quality information on the produced polymer corresponding to a first time point, and storing priority information of raw materials corresponding to each of a plurality of types of quality information included in the quality information and target value information corresponding to each of the plurality of raw material types of quality information, the plurality of types of quality information including at least one of a melting index (MI) value, a density value, and a melt flow index (MFR) value of the produced polymer;

acquiring the input raw material information corresponding to the first time point before a preset time elapses from a second time point and process status information corresponding to the first time point based on the process history information of the polymer production apparatus, when process information including input raw material information, polymer production information, and process status information corresponding to the second time point is received from the polymer production apparatus;

using the input raw material information corresponding to the first time point, the process status information corresponding to the first time point, and the polymer production information corresponding to the second time point to update the input raw material information corresponding to the second time point and the process status information corresponding to the second time point, the updating of the input raw material information corresponding to the second time point is reflecting an amount of recovered raw materials among an amount of input raw materials at the first time point in an amount of input raw materials at the second time point;

using the updated input raw material information and the updated process status information to identify predicted process information including predicted polymer production information at a third time point when a preset time elapses from the second time point;

inputting the updated input raw material information, the updated process status information, and predicted polymer production information at the third time point to the trained neural network model to acquire predicted quality information of the polymer corresponding to the third time point;

acquiring guide information that guides a difference between the acquired predicted quality information and the target value to be less than a preset value based on priority information of the raw materials when the acquired predicted quality information differs from the target value by more than the preset value; and providing a user interface (UI) including the acquired guide information, wherein the UI includes at least one of the process history information, the predicted quality information of the polymer corresponding to the third time point, trend information corresponding to each of the plurality of types of quality information, explanatory function information corresponding to each of the plurality of types of quality information, and control variable guidance information corresponding to each of the plurality of types of quality information.

7. The control method of claim 6, wherein the process history information includes input raw material information, polymer production information, process status information, and quality information of the produced polymer corresponding to each of a plurality of time points before the second time point, and the trained neural network model is trained to output the predicted quality information when the process information including the input raw material information, the polymer production information, and the process status information and the predicted polymer production information are input.

8. The control method of claim 6, wherein the UI further includes process information corresponding to the second time point.

9. The control method of claim 8, wherein the acquiring of the guide information further includes:

identifying sub-process information in which the input raw material information changes among the information included in the received process information corresponding to the second time point;

identifying sub-predicted process information based on the sub-process information;

inputting the sub-process information and the sub-predicted process information to the trained neural network model to acquire at least one piece of sub-predicted quality information corresponding to the third time point; and using the acquired predicted quality information and the acquired at least one piece of sub-predicted quality information to acquire the guide information.

10. The control method of claim 8, further comprising:

identifying control information corresponding to the received user input, when a user input corresponding to the acquired guide information is received; and transmitting the identified control information to a control engine.

11. A non-transitory computer-readable recording medium for storing computer instructions causing an electronic device for implementing a quality prediction and control system to perform operations when executed by a processor of the electronic device, wherein the operations includes:

storing, in a memory, process history information of a polymer production apparatus, the process history information including input raw material information, polymer production information, process status information, and quality information on the produced polymer corresponding to a first time point, and storing priority information of raw materials corresponding to each of a plurality of types of quality information included in the quality information and target value information corresponding to each of the plurality of types of quality information, the plurality of types of quality information including at least one of a melting index (MI) value, a density value, and a melt flow index (MFR) value of the produced polymer;

acquiring the input raw material information corresponding to the first time point before a preset time elapses from a second time point and process status information corresponding to the first time point based on the process history information of the polymer production apparatus, when process information including input raw material information, polymer production information, and process status information corresponding to the second time point is received from the polymer production apparatus;

using the input raw material information corresponding to the first time point, the process status information corresponding to the first time point, and the polymer production information corresponding to the second time point to update the input raw material information corresponding to the second time point and the process status information corresponding to the second time point, the updating of the input raw material information corresponding to the second time point is reflecting an amount of recovered raw materials among an amount of input raw materials at the first time point in an amount of input raw materials at the second time point;

using the updated input raw material information and the updated process status information to identify predicted process information including predicted polymer production information at a third time point when a preset time elapses from the second time point;

inputting the updated input raw material information, the updated process status information, and predicted polymer production information at the third time point to the trained neural network model to acquire predicted quality information of the polymer corresponding to the third time point;

acquiring guide information that guides a difference between the acquired predicted quality information and the target value to be less than a preset value based on priority information of the raw materials when the acquired predicted quality information differs from the target value by more than the preset value; and providing a user interface (UI) including the acquired guide information, and the UI includes at least one of the process history information, the predicted quality information of the polymer corresponding to the third time point, trend information corresponding to each of the plurality of types of quality information, explanatory function information corresponding to each of the plurality of types of quality information, and control variable guidance information corresponding to each of the plurality of types of quality information.

* * * * *